United States Patent [19]

Petusky

[11] Plant 4,311

[45] Oct. 10, 1978

[54] CHRYSANTHEMUM PLANT NAMED AMBER CONCORD

[75] Inventor: Kerry S. Petusky, West Chicago, Ill.

[73] Assignee: Pan-American Plant Company, West Chicago, Ill.

[21] Appl. No.: 795,309

[22] Filed: May 9, 1977

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Chas. W. Rummler

[57] ABSTRACT

A new cultivar of potted chrysanthemum characterized by the amber-bronze color of its relatively small, composite and single type flowers which can be brought to bloom the year around with a consistent 9-week response under photoperiod control, the flower color ranging from a green-yellow to bronze-yellow to aureolin depending upon the season of flowering under normal greenhouse conditions for commercial flowering plant production.

3 Drawing Figures

BACKGROUND OF THE NEW PLANT

My new chrysanthemum plant was discovered by me in August 1974 as a sport of Pink Concord (U.S. Plant Pat. No. 4,120) being grown under glass at West Chicago, Ill. The attractive coloring of this sport prompted me to reproduce it by cuttings from the flowering stem. Further propagation of the new plant through successive generations by vegetative cuttings at West Chicago, Ill., and causing selected plants so produced to be flowered at various times throughout a span of about two years has demonstrated that the new and distinctive characteristics of this plant hold true from generation to generation and appear to be firmly fixed.

Commercial scale propagation of this new plant is now being done by means of vegetative cuttings at West Chicago, Ill., and at Cortez, Fla.

DESCRIPTION OF THE DRAWINGS

This new chrysanthemum cultivar is illustrated by the accompanying drawings, one sheet of which is a print of a photograph showing a potted plant in full bloom and in full color, the photograph having been made in January 1977, and the second sheet being a print of a machine copy of typical leaves from the new plant. The color shown photographically is believed to be as nearly true as it is reasonably possible to obtain by conventional photographic procedures.

DESCRIPTION OF THE NEW PLANT

The following is a detailed description of my new chrysanthemum cultivar with color designations according to the R.H.S. Colour Chart published by the Royal Horticultural Society of London, England.

THE PLANT

Origin: Sport.

Parentage: Pink Concord (U.S. Plant Pat. 4,120).

Classification:

*Botanic.*—*Chrysanthemum morifolium.*

*Commercial.*—Greenhouse pot plant.

Form: Perennial herbaceous bush.

Height: 10 to 12 inches.

Growth: Terminal. Vigorous and upright, sturdy and with good strength.

Branching: Under natural conditions.

Foliage: Abundant, with six to eight leaves per 4 inches of stem.

*Leaf size.*—When mature—2½ to 3½ inches long and 1⅛ to 1⅞ inches wide.

*Leaf shape.*—Lobed and slightly serrated.

*Surface aspect.*—Canescent.

*Color.*—Upper side—137A. Under side—146A.

*Venation.*—Pinnate.

*Petioles.*—Length — ½ to ⅝ inch.

THE BUD

Form: Almost global.

Size: ⅜ to 7/16 inch in diameter and ¼ inch in depth.

Opening rate: The bud opens slowly.

Color: When phyllaries first divide — 144A. When florets begin to unfurl — 162A, 163A, 163B.

Phyllaries: The outside of the receptacle has many involucral bracts which are spear-shaped and upstanding.

*Color.*—Inside—137C. Outside — 137C.

*Surface aspect.*—Pubescent.

Peduncle: Erect and 1½ to 3 inches long.

*Surface aspect.*—Pubescent.

THE FLOWER

Recommended flowering: The year around with photoperiod control.

Response: 9 weeks.

Natural flowering season: October 20 to 27.

Blooms: Flower type — composite and single.

*Size.*—Small. Diameter 2 to 2½ inches. Depth: ⅝ to ⅞ inch.

*Borne.*—A head of many florets carried on a receptacle.

*Shape.*—Flat.

*Florets.*—Numerous in number. Form: Disc florets — short, thin and linear. Ray florets — long-linear with obtuse apex.

| Color | Jan. | Feb. | Mar. | Apr. | Sep. | Nov.–Dec. |
|---|---|---|---|---|---|---|
| Ray florets: | | | | | | |
| Top side | 14A | 13B | 17B–21B | 163B | 163B | 12A |
| Under side | 14C | 12B | 20B–21D | 162A | 162B | 11A |

*Disc florets.*—The center florets of the disc are Green 144A from which the floret colors gradually approach a Golden Yellow 17A at the outer margin of the disc. Firmness: Medium. Appearance: Very slight shine. Discoloration: Slight fade after full bloom. Persistence: The florets hang on and dry.

*Peduncle.*—Upright and sturdy. Length: 1½ to 3 inches. Color: 137C.

*Fragrance.*—None.

*Lasting quality.*—On plant: 3 weeks. As cut flower: Not recommended.

REPRODUCTIVE ORGANS

Stamens: Arrangement — syngenesious.

*Number.*—5.

*Filaments.*—1/16–⅛ inch long. Color: Light yellow.

*Pollen.*—Color — Yellow.

Pistils: Number — one to each ray and disc floret.

*Length.*—3/16 to ¼ inch.

*Stigmas.*—Color — Yellow.

Ovaries: Inferior bicarpellate in character.

This new chrysanthemum cultivar is very similar to its parent Pink Concord in all characteristics except color and in that respect the new plant is unique. Also the flower color of the new plant changes during the course of the year according to the season of flowering, the higher light intensities and longer days of summertime, as well as warmer climate, resulting in blooms having a considerably darker or bronze yellow coloration than those flowered in the winter months when the colors vary from a green yellow to aureolin. Thus variation of light intensity or temperature, or both, while bringing this plant to flower will result in corresponding color variations as indicated by the color chart shown above.

I claim:

1. A new and distinct cultivar of chrysanthemum plant, substantially as herein shown and described, characterized by the light yellow to bronze color variation of its relatively small, composite flowers due to its susceptibility to changes of blossom color under variations of light and temperature conditions.

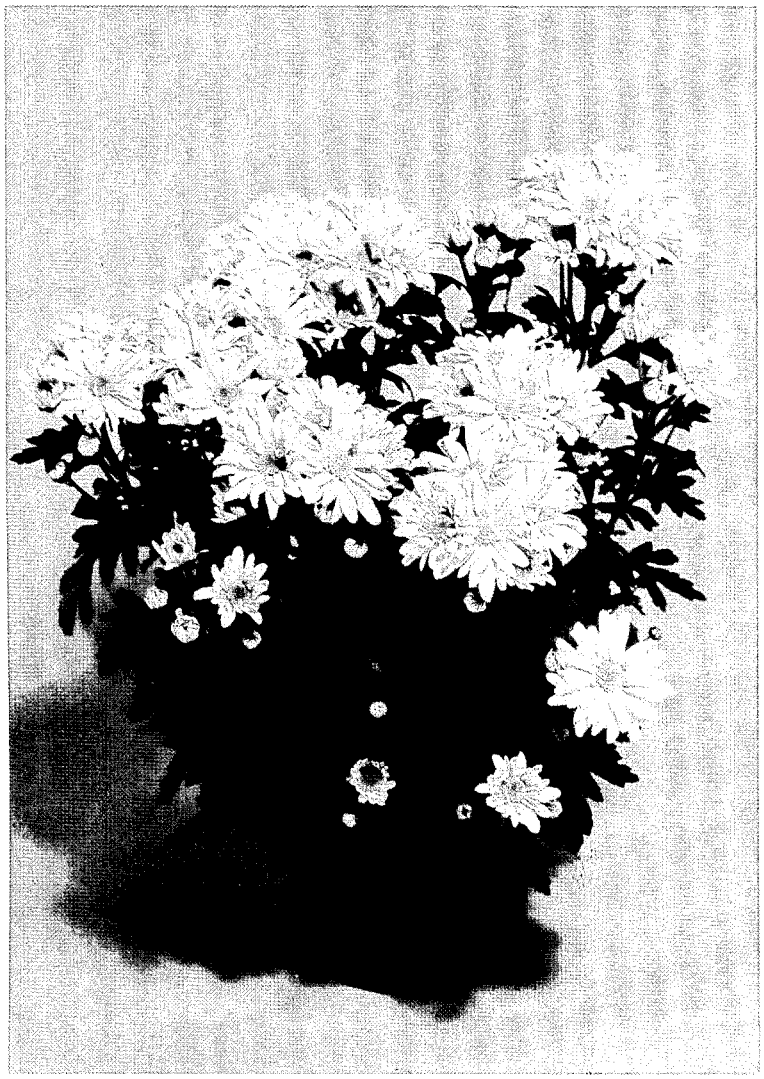

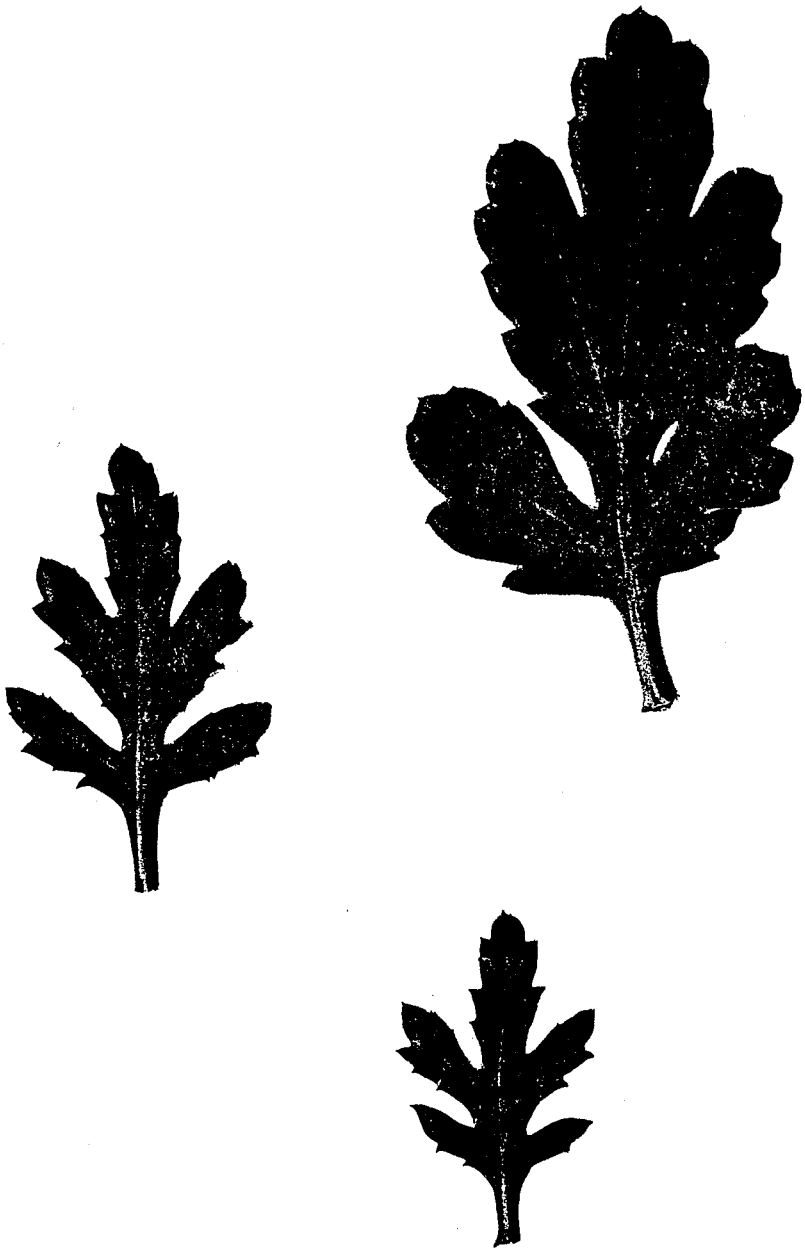

* * * * *